United States Patent [19]
DeLuca et al.

[11] Patent Number: 5,086,779
[45] Date of Patent: Feb. 11, 1992

[54] BACK ANALYSIS SYSTEM

[75] Inventors: Carlo J. DeLuca; L. Donald Gilmore, both of Wellesley; Serge H. Roy, Duxbury, all of Mass.

[73] Assignee: Trustees of Boston University, Boston, Mass.

[21] Appl. No.: 530,302

[22] Filed: May 30, 1990

[51] Int. Cl.$^5$ .......................................... A61B 5/0488
[52] U.S. Cl. ..................................... 128/733; 128/774
[58] Field of Search ................ 128/733, 774, 781, 905

[56] References Cited

U.S. PATENT DOCUMENTS

| | | | |
|---|---|---|---|
| 4,667,513 | 5/1987 | Konno | 73/379 |
| 4,708,148 | 11/1987 | Olson | 128/781 |
| 4,912,638 | 3/1990 | Pratt, Jr. | 364/413.02 |

Primary Examiner—Kyle L. Howell
Assistant Examiner—Kevin Pontius
Attorney, Agent, or Firm—John E. Toupal; Harold G. Jarcho

[57] ABSTRACT

A muscle function analysis system including a base; a restraint device supported by the base and shaped and arranged to receive and immobilize a human body portion retaining a muscle group concurrently activatable to produce a body function; and a support apparatus supported by the base and shaped and arranged to support other portions of the body, the support apparatus adapted to substantially isolate activity in the muscle group from muscle activity in the other body portions. Also included are an electrode array adapted for coupling to the muscle group so as to receive myoelectric signals generated by muscle activity therein and a processing system coupled to the electrode array and adapted to process the myoelectric signals. By isolating muscle activity in a particular muscle group, more useful data is obtained for evaluating muscle dysfunction in the group.

22 Claims, 4 Drawing Sheets

BACK ANALYSIS SYSTEM

LICENSE RIGHTS

The U.S. Government has a paid-up license in this invention and the right in limited circumstances to require the patent owner to license others on reasonable terms as provided for by the terms of Grant No. B391-2R awarded by Rehabilitation Research and Development Service of the Department of Veteran Affairs.

BACKGROUND OF THE INVENTION

Lumbar muscle function is considered to be an important component of chronic lower back pain (LBP). It has been found that individuals with endurable back muscles and general physical fitness have fewer incidences of back problems than deconditioned cohorts. Complementary studies have documented compromised muscle function in patients with LBP. Although the mechanism associating muscle insufficiency to LBP is not clearly understood, it is commonly held that the passive tissues of the spine are increasingly stressed with increasing functional muscle insufficiency. The high incidence of back injury among workers exposed to fatiguing manual tasks and whole body vibration lend support to this concept. To further understand the relationship of muscle function to LBP, more effective assessment procedures need to be developed and tested for clinical use.

Most techniques presently available to assess muscle deficiencies are either nonobjective or they lack rigorous clinical validation and reliability. One technique that does provide objective data entails electromyographic (EMG) spectral analysis of lower back muscles. Although providing advantages over other techniques, prior EMG systems have suffered certain deficiencies resulting primarily from treatment of individual muscle groups as a continuous muscle mass and exclusive reliance on the amplitude of EMG signals. Improved but less than fully satisfactory techniques utilizing EMG spectral measurements are disclosed in Gilmore L. D., DeLuca D. J.; Muscle fatigue monitor: Second generation. IEEE Trans Biomed Eng BME-32: 75-78, 1985. Prior disclosures of EMG spectral analysis of LBP include Roy, S. H., DeLuca, C. J., Gilmore, L. D.: Computer Aided Back Analysis System. IEEE Engineering in Medicine and Biology Society—10th Annual International.

The object of this invention, therefore, is to provide an improved system for analyzing muscle fatigue associated with LBP.

SUMMARY OF THE INVENTION

This invention is a muscle function analysis system including a base; a restraint device supported by the base and shaped and arranged to receive and immobilize a human body portion retaining a muscle group concurrently activatable to produce a body function; and a support apparatus supported by the base and shaped and arranged to support other portions of the body, the support apparatus adapted to substantially isolate activity in the muscle group from muscle activity in the other body portions. Also included are an electrode array adapted for coupling to the muscle group so as to receive myoelectric signals generated by muscle activity therein and a processing system coupled to the electrode array and adapted to process the myoelectric signals. By isolating muscle activity in a particular muscle group, more useful data is obtained for evaluating muscle dysfunction in the group.

According to one feature of the invention, the one body portion includes a body joint, the muscle group is activatable to produce torque at the joint, and the restraint device establishes a predetermined angular orientation of the joint. Muscle activity isolation is enhanced by selectively establishing a particularly desirable joint orientation.

According to another feature of the invention, the one body portion of a human body is the pelvis, and the joint is between the pelvis and the torso. Immobilization of the pelvis facilitates an analysis of LBP.

According to yet another feature of the invention, the restraint device comprises plural molds adapted to envelop the one body portion and adjustable connector means for selectively fixing the relative positions between the plural molds. The provision of adjustable plural molds enhances use of the system with diverse test subjects.

According to still other features of the invention, the support apparatus includes a knee support adapted to maintain the body's knee joints in flexion, and a foot support adapted to maintain the body's ankle joints in plantarflexion. The knee and foot supports enhance operation by establishing a postural position with the thigh muscles at rest.

According to a further feature of the invention, the restraint device is adapted to permit establishment of an adjustable posterior pelvic tilt. The posterior pelvic tilt combines with partial knee flexion established by the knee support to substantially reduce or actually inhibit use of hamstring muscles during back extension.

According to an additional feature of the invention, the system includes a force constraint supported by the base and adapted to engage and prevent movement of the body's torso during extension thereof. The constraint permits a test subject to introduce contraction of the muscles in the lower back.

According to still other features of the invention, the base includes a substantially vertical standard and a pedestal adapted to support the body's feet; and the restraint device includes a first coupling providing a given spacing between the standard and an upper portion of the molds, a second coupling providing a predetermined spacing between the standard and a lower portion of the molds, and an adjustment means for selectively adjusting the predetermined spacing relative to the given spacing. This arrangement facilitates the desirable establishment of a posterior pelvic tilt.

According to additional features of the invention, the knee support is supported by the standard and defines knee support surfaces forming an acute angle with the standard so as to maintain the body's knee joints in flexion; and the foot support is supported by the pedestal and defines a surface inclined at an acute angle with respect to the horizontal so as to maintain the body's ankle joints in plantarflexion. This arrangement facilitates desired postural orientation with a test subject in a desirable upright position.

DESCRIPTION OF THE DRAWINGS

These and other objects and features of the invention will become more apparent upon a perusal of the following description taken in conjunction with the accompanying drawings wherein.

DESCRIPTION OF THE PREFERRED EMBODIMENT

Figure 1:
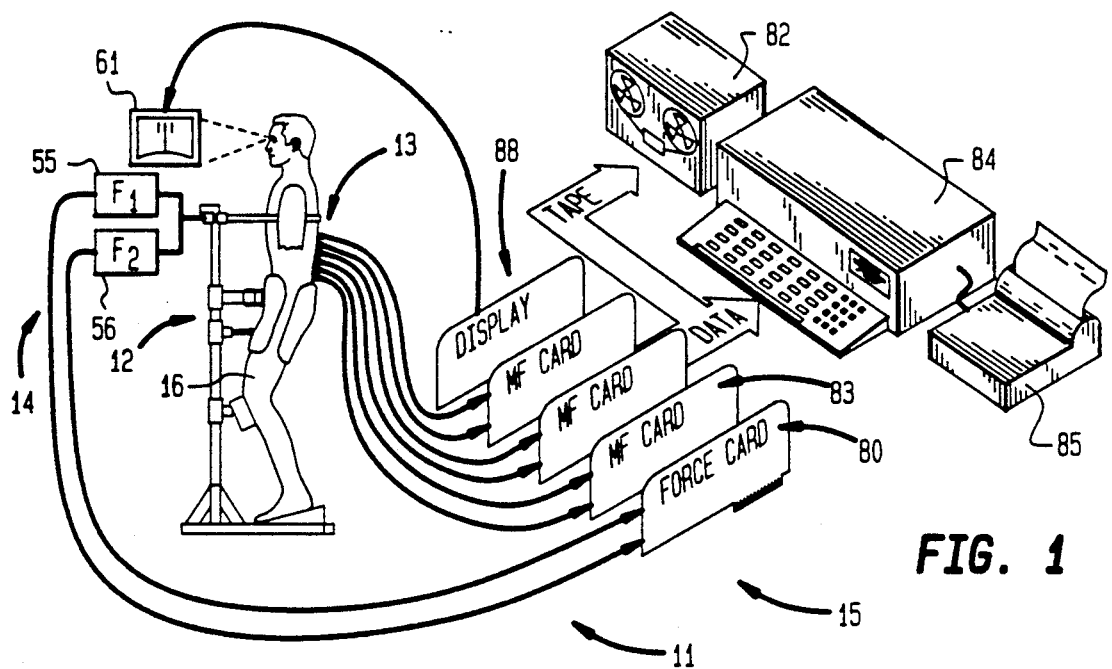
FIG. 1 is a block circuit diagram illustrating a back muscle analysis system according to the invention.

A back muscle analysis system 11 includes a postural control device 12, an EMG detecting electrode array 13, a visual applied-force feedback system 14 and a signal processing system 15. After being immobilized in the postural control device 12, a test subject 16 generates desired isometric back muscle activity, parameters of which can be monitored by the applied force feedback system 14. Resultant EMG signals are detected by the electrode array 13 and fed into the signal processing system 15. An analysis of back muscle dysfunction is obtained by analyzing various parameters of the EMG signals determined by the processing system 15.

Figure 2:
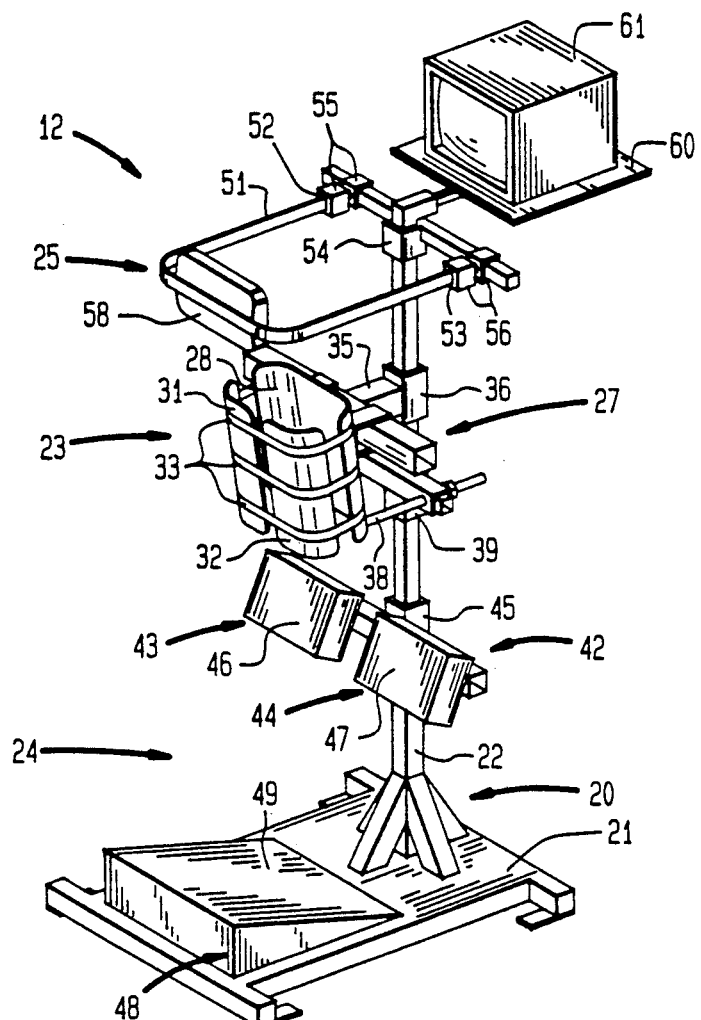
FIG. 2 is a perspective view of a postural positioning device employed with the system shown in FIG. 1.

As shown in FIG. 2, the postural control device 12 includes a base unit 20 consisting of a pedestal 21 and a vertical standard 22. Also included in the control assembly 12 is a subject restraint assembly 23, a subject support assembly 24 and a force constraint harness 25 all supported by the base 20. The restraint assembly 23 consists of a mold assembly 26 secured to the standard 22 by a coupling assembly 27. Forming the mold assembly 26 are a posterior mold portion 28 and a pair of anterior mold portions 31, 32. A plurality of adjustable straps 33 secure the anterior molds 31, 32 to the posterior mold 28 in an adjustable configuration. Forming the coupling assembly 27 is a first coupling consisting of a bar 35 extending transversely from the standard 22 and having opposite ends attached to, respectively, an upper portion of the posterior mold portion 28 and a vertically adjustable collar 36 on the standard 22; and a second coupling consisting of a rod 38 extending transversely from the standard 22 and having one end engaging a lower portion of the posterior mold portion 28 and an opposite end attached to a vertically adjustable collar 39 on the standard 22. A nut 41 engaged with the threaded rod 38 permits horizontal adjustment thereof relative to the standard 22.

The subject support assembly 24 includes a knee support assembly 42 having right and left knee pads 43, 44 extending transversely from the standard 22 and supported thereon by a vertically adjustable collar 45. The right and left knee pads 43, 44, define, respectively, knee support surfaces 46, 47 oriented at an acute angle to the standard 22. Also included in the subject support assembly 24 is a foot support block 48 having an in-clined foot support surface 49 also oriented at an acute angle to the vertical standard 22.

The force constraint harness 25 consists of a flexible strap 51 having opposite ends 52, 53 secured to a vertically adjustable mount 54 on the standard 22. Connecting the ends 52, 53, respectively, to the mount 54 is a pair of load detecting transducers 55, 56 such as conventional load cells. A pad 58 is attached to a central portion of the flexible strap 51. Extending transversely from an upper end of the standard is a support bracket 60 that supports a video display 61.

Figure 3:
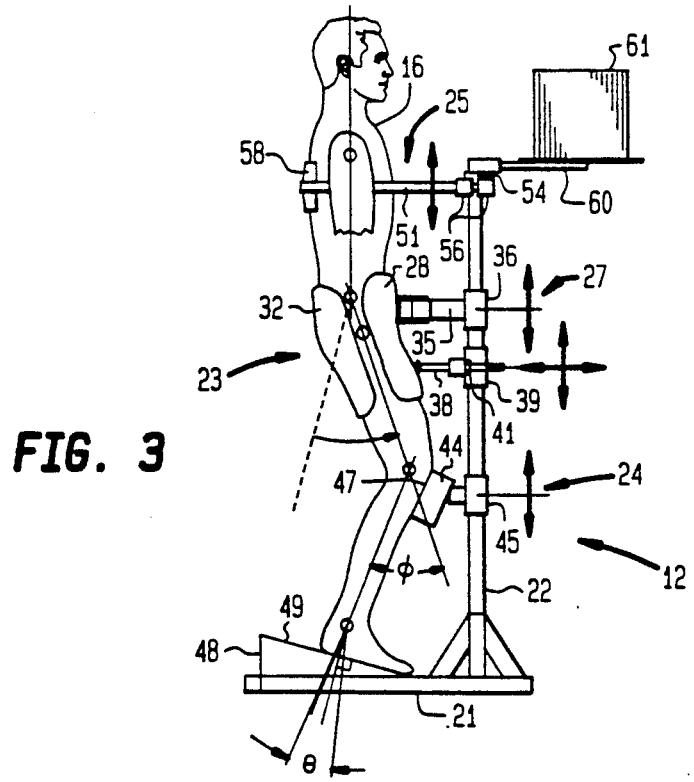
FIG. 3 is a schematic diagram depicting a test subject restrained in the device shown in FIG. 2.

After placement of the electrode array 13 in the manner described hereinafter, the subject 16 is immobilized in the control device 12 as illustrated in FIG. 3. A body portion retaining the lower back muscles of the subject 16 is received and immobilized by the restraint assembly 23. Specifically, the posterior and anterior mold portions 28, 31 and 32 are adjusted and secured by the connective straps 33 to conform to and envelop the hip, upper thigh, buttocks and anterior pelvic regions of the subject's body. Selective rotation of the nut 41 adjusts the effective length of the rod 38 and a predetermined spacing established thereby between the standard 22 and a lower portion of the posterior mold 28. The predetermined spacing is adjusted with respect to the given spacing established by the first coupling bar 35 between the upper portion of the posterior mold portion 28 and the standard 22. In that manner, the normal anterior pelvic tilt of the subject 16 is changed to a full posterior tilt of desired value as illustrated in FIG. 3. The knees of the subject 16 are placed in engagement with the pads 43, 44 which provide patellar tendon bearing surfaces and maintain the subject's knee joints in flexion at an angle $\phi$ preferably between 10° and 35°. Supporting the feet of the subject 16 is the inclined surface 49 of the block 48 that maintains the subject's ankle joints at an angle $\theta$ preferably between $\pm 10°$ plantarflexion. That orientation prevents the feet from slipping posteriorly during a contraction of the back. Finally, the force restraint harness 25 is activated by placing the flexible strap around the subject 16 with the pad 58 engaging the subject's upper back portion. The mount 54 and the collars 36 and 45 are adjusted to establish desired vertical positions for, respectively, the force constraint harness 25, the restraint assembly 23 and the knee support assembly 43 as determined by the specific physical characteristics of the subject 16.

Figure 4:
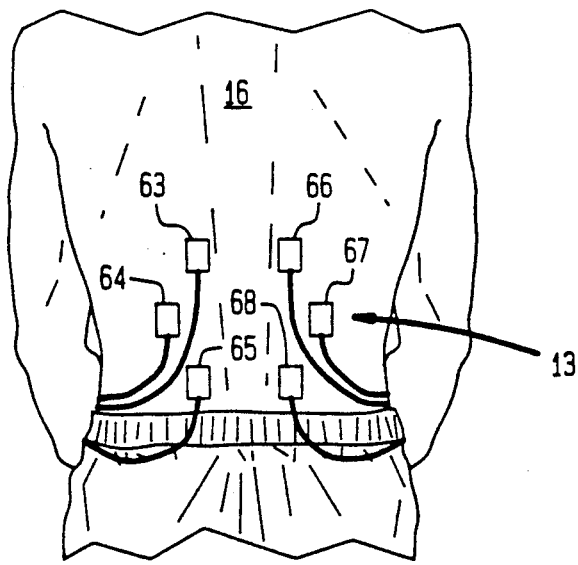
FIG. 4 is a diagram illustrating electrode placement on back muscles of a test subject.
Figure 5:
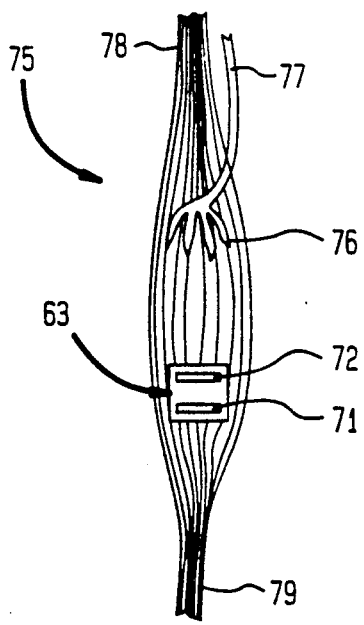
FIG. 5 is a diagram illustrating orientation of an electrode over a muscle.

Prior to positioning the subject 16 in the postural control assembly 12, the electrode array 13 coupled to the processing system 15 is carefully arranged over the subject's lower back region as shown in FIG. 4. The array 13 consists of a first set of surface electrodes 63-65 and a second set of surface electrodes 66-68 bilaterally placed over specific muscles of the subject's lower back. In a preferred application, the electrodes 63, 66 are bilaterally located over the multifidus muscle at the L5 spinal level, the electrodes 64, 67 are bilaterally located over the iliocostalis lumborum muscle at the spinal level L2 and the electrodes 65, 68 are bilaterally placed over the longissimus thracis muscle at the spinal level L1. Preferably each of the electrodes 63-68 is adapted for surface attachment over a muscle and includes a pair of elongated, substantially parallel detection surfaces 71, 72 as illustrated in FIG. 5. Surface electrodes of a type suitable for use in the system 11 are disclosed in Gilmore, L. D. and DeLuca C. J.: Muscle Fatigue Monitor: Second generation, IEEE Trans Biomed Eng. BME-32: 75-78, 1985.

To isolate myoelectric activity detected by the electrode 63 to that produced in the specific muscle 75 over which it is placed, and to thereby minimize "cross-talk" produced by muscle activity in adjoining muscles, the detection parallel surfaces 71, 72 are preferably oriented substantially perpendicular to the muscle fibers as shown in FIG. 5. In addition, the electrode 63 is placed in a position spaced substantially from the innervation zone (motor point) 76 at the end of a nerve 77 associated with the muscle 75 and substantially spaced from the tendons 78, 79 attached to the muscle 75. The other electrodes 64-68 are similarly positioned to enhance detected signal quality. During strategic placement of the electrodes 63-68, the specific muscles to be covered thereby are electrically stimulated and palpitated to accurately determine fiber orientation and motor point locations.

After being positioned in the postural control device 12, the subject 16 exerts a posterior force (i.e. trunk extension) against the constraint harness 25 producing a static (isometric) contraction of the lower back muscles being monitored by the electrodes 63-68. The EMG signals detected by the electrodes 63-68 are fed into the processing system 15 and analyzed to determine certain parameters thereof. Those parameters can then be used to access muscle dysfunction in the manner described hereinafter. In addition, the constraint harness 25 separates the force generated by the subject 16 into two components F1, F2 that are sensed by the load cells 55, 56. Outputs produced by the sensors 55, 56 are applied to a force monitoring section 80 which produces inputs to the video display 61. In response to the displays provided by the video 61, the subject 16 is able to maintain applied force at desired levels and to control symmetry between F1 and F2.

Included in the processing system 15 are an amplifier section for amplifying the EMG signals, a recorder 82 for recording signal values, a muscle fatigue monitor (MF) 83 for monitoring the signals, a computer 84 and a printer-plotter unit 85. Also included is the force monitoring section 80 including a differential amplifier that receives the outputs of the transducers 55, 56 and a display section 88 providing an input to the video 61. A further description of the processing system 15 can be found in Gilmore, L. D., DeLuca, C. J.: Muscle Fatigue Monitor: Second generation, IEEE Trans Biomed Eng BME-32: 75-78, 1985 and Gilmore, L. D., DeLuca, C. J.: Muscle fatigue monitor (MFM): An IBM-PC based measurement system. Presented at the 9th annual meeting of the IEEE-EMBS, Boston, Mass., Nov. 14, 1987.

The six channels of EMG signals provided by the electrodes 63-68 are amplified in the amplifier section 81 to achieve an output amplitude of 2 to 3 V peak-to-peak. This data is recorded by the tape recorder 82. In addition, the outputs of the transducers 55, 56 are recorded by the recorder 82. The MFM calculates the median frequency (MF) and the root-mean-squares (RMS) of each received EMG signal in real-time using analog circuitry. Median frequency is defined as the frequency that separates the power density spectrum into halves of equal power. This parameter provides a reliable, consistent, and unbiased measure of the frequency shift of the EMG signal associated with muscle fatigue during sustained, constant-force contractions. In addition, the computer 84 utilizes input from the transducers 55, 56 to calculate for each subject a maximum voluntary contraction (MVC) by averaging force values over an adjustable window. The MVC force value is stored and can be used to set the visual display 61 to the desired percentage of the MVC. The feedback display helps the subject maintain a constant level of contractile force.

During each test of a subject, back muscle endurance characteristics are measured by assessing how rapidly the muscle groups monitored by the electrodes fatigue. This is followed by an assessment of how capable the muscles are of recovering to their pre-fatigued state. Fatigue is induced by having the subject contract their back muscles to produce a static (isometric) contraction at a specified force level which is a percent of MVC. This contraction is sustained for a specified period of time (for example, 15 seconds to 1 minute) or else repeatedly (on-and-off) for a specified duty cycle (e.g. 10 seconds of contraction followed by 5 seconds of rest repeated for 1 hour). The contraction levels can be specified at a pre-determined % MVC depending on the desired intensity of the fatigue task. Both the "static" and "dynamic" trials result in a state of fatigue in the lower back muscles which are measured by the EMG. Following the fatigue state, the ability of the muscle(s) to return to their rested or baseline level is monitored by having the subject rest (usually 1, 2, 5 or 10 minutes) and then retested briefly (10 second duration) to monitor the EMG parameters at specific times into recovery.

Following each test, the EMG signals provided by the electrodes 63-68 are individually processed by analog circuitry using the muscle fatigue monitor (MFM) 83 to compute the MF value of the signal. This parameter and the force data from the transducers 55, 56 are further amplified and simultaneously digitized by the computer 84. A sampling rate of 10 Hz is used to satisfy the Nyquist criterion, since the fluctuations of the MF and force are below 4 Hz due to the characteristics of the MFM.

Figure 6:
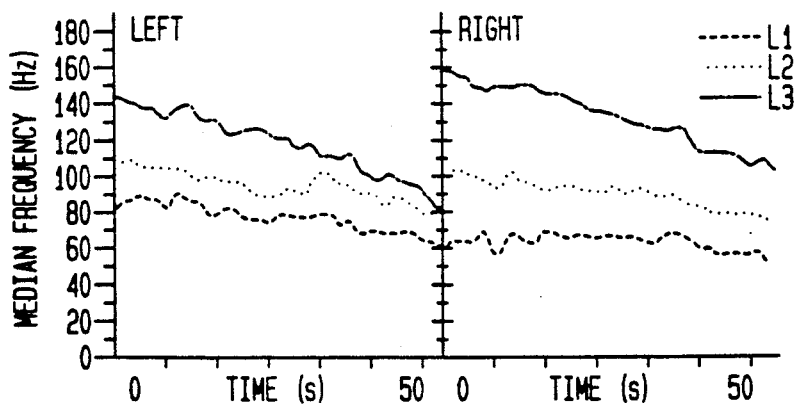
FIG. 6 is a diagram in which median frequency of myoelectric signals is plotted as a function of muscle contraction duration.
Figure 7:
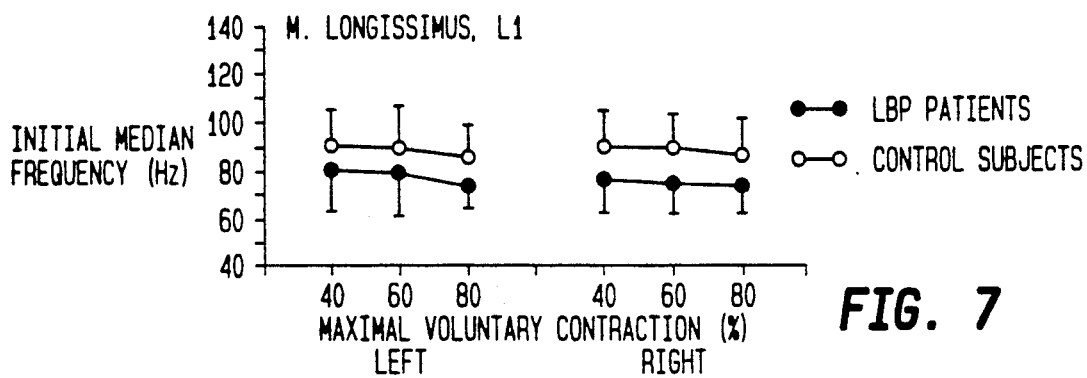
FIGS. 7-9 are diagrams in which the initial median frequency of myoelectric signals is plotted as a function of % maximum voluntary contraction (MVC) forces produced by the system of FIG. 1.
Figure 8:
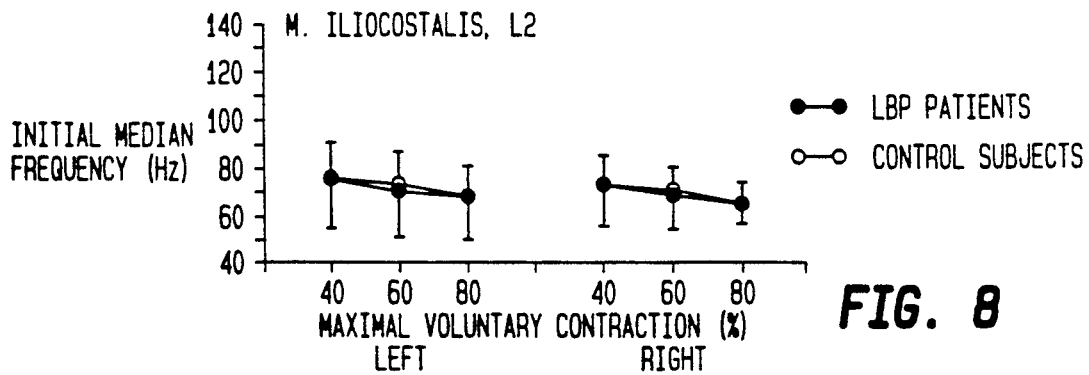
Figure 9:
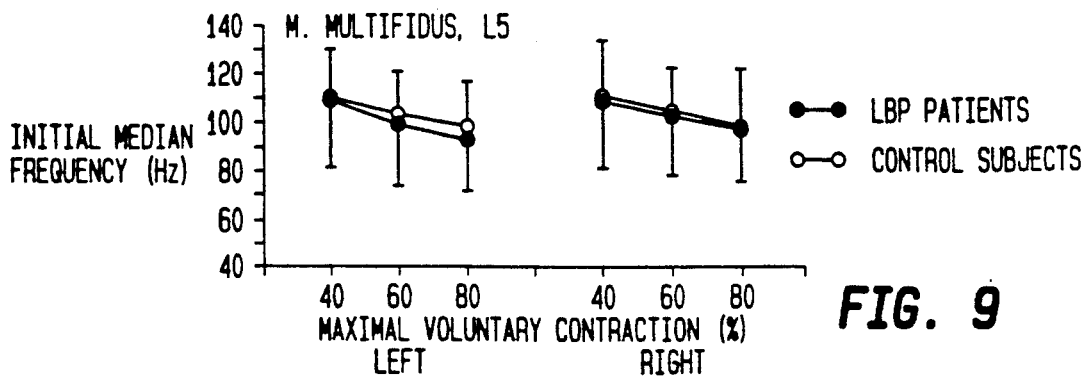
Figure 10:
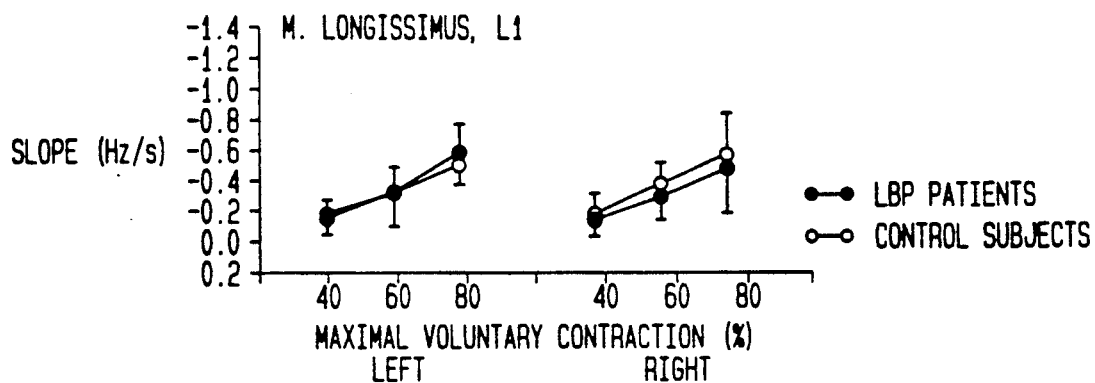
FIGS. 10-12 are diagrams in which the mean slope of the median frequency of myoelectrical signals is plotted as a function of % MVC forces produced by the system shown in FIG. 1.
Figure 11:
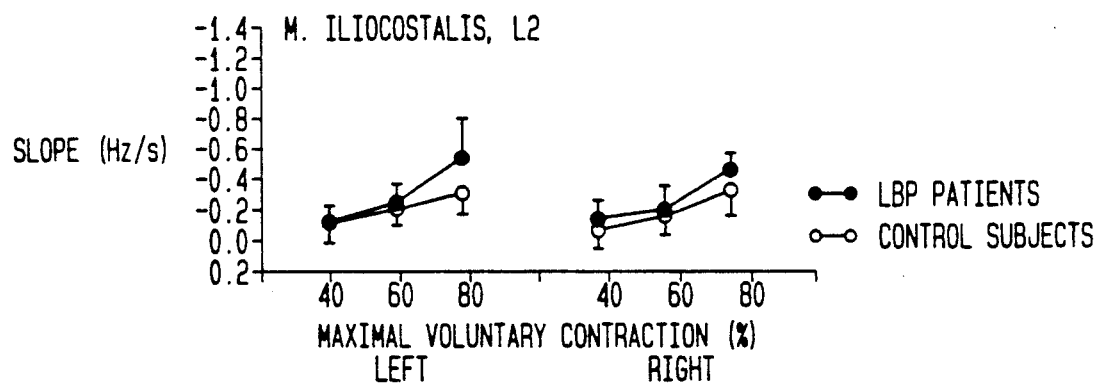
Figure 12:
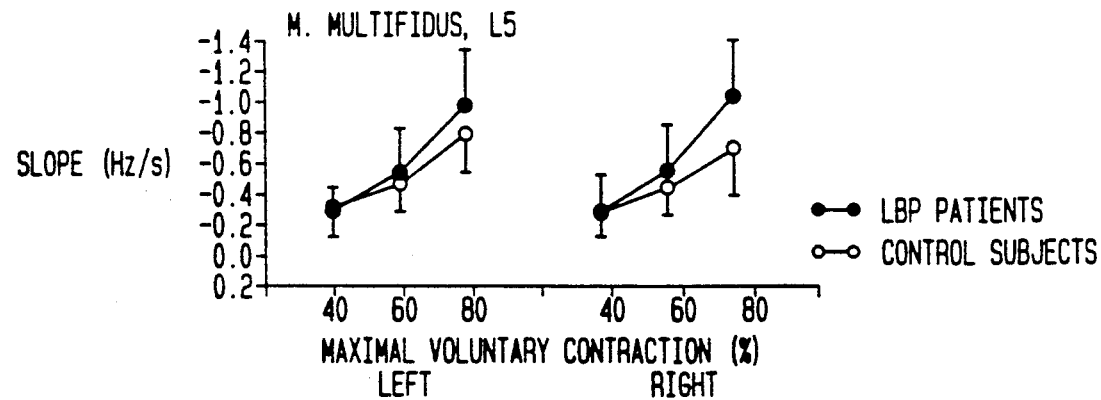

The digitized MF records for each of the six electrodes 63-68 are simultaneously plotted in the section 85 as a function of time (FIG. 6). The software algorithm uses a moving average filter with a 2-second window (200 samples) to reduce high-frequency fluctuations in the data. These high-frequency fluctuations are due to the stochastic nature of the EMG signal and are not of interest when observing the time-dependent changes of the MF associated with fatigue. The plot is divided into two sections, corresponding to outputs of the electrodes 63, 64, and 65 on the left side of the back and the outputs of the electrodes 66, 67 and 68 on the right side of the back. The vertical axis represents the MF and the horizontal axis represents time. Quantitative measurements of the time rate of change of the MF of the individual curves is also provided. Linear regression using the method of least squares is used to compute the rate of decrease of the MF. A linear fit to the unfiltered data is chosen since it most consistently represents the time-dependent change of the MF as monitored from the back extensor muscles. The following parameters are investigated by the computer 84: 1) The initial median frequency (IMF) of the curve. This value is obtained by calculating the y-intercept of a straight line regression fit by a "least-squares" method to the MF data. 2) The slope of the regression line for the MF-time function, calculated over the duration of a muscle contraction.

In a preferred application of the analysis system 11, a suitable number of control subjects are first sequentially analyzed in the manner described above to provide a normative control data base. Subsequently, that data base is compared with EMG signal parameters determined by the signal processing system 15 during analysis of a test subject to locate dysfunctional lower back muscles.

In a specific example, twelve patients with a history of chronic back pain were evaluated and compared with a control group of 12 healthy subjects. All participants were male and right-handed. Grouping was determined by the presence or absence of a documented history of chronic back pain. Chronicity was defined as persistent or frequently recurring pain over a period of at least one year. The average duraction of a LBP history was 5.2 years for the patient group (range 1.5-13 years). Patients with acute exacerbation of back pain were excluded. Those subjects with previous back surgery or radiographic evidence of structural disorders of the spine also were excluded.

Following the determination of each subject's MVC and a 5-minute rest, the subject performed three constant-force contractions at 40% MVC, 60% MVC, and 80% MVC for a duration not to exceed 1 minute. A 15-minute rest period between contractions allowed for full recovery of the MF parameters. The summary statistics for IMF and MF slope measures were plotted as shown in FIGS. 7-9 and 10-12, respectively. Each contains data for the longissimus (L1), iliocostalis (L2) and multifidus (L5) muscle detection sites. In each plot, the data from the left and right sides of the back are further subdivided, as are the force levels of the contraction. This graphical representation identifies a number of important results, which are summarized below:

1) The IMF decreases for increasing levels of contractile force. This relationship was present for all muscle groups tested and in both LBP subjects and control subjects.

2) Left-right differences are present in both LBP and control subjects for each of the parameters studied.

3) For any given contraction force level, the average IMF and MF slope are greater at the L5 detection site than at either the L1 or L2 detection sites for both LBP and control subjects.

4) The IMF is significantly lower for LBP subjects compared with control subjects across all force levels of left and right longissimus, L1 electrode location.

5) Low-back pain subjects exhibit significantly higher MF slope values than control subjects at 80% MVC for the L2 and L5 recording sites.

After establishing a data base, the system 11 is used diagnostically to identify by quantifiable and objective methods whether an individual test subject has a muscular component to their low back pain problem. This task involves a comparison of the data base with the results obtained during a test of the test subject in the manner described above. The quantifiable technique also provides a measure of the degree of certainty of the diagnosis. This is accomplished by analyzing the EMG spectral parameter data from a fatigue test using discriminant analysis procedures. This statistical procedure establishes a formula that best separates the data into a Low Back Pain and non-Low Back Pain group. The formula can then be used to determine whether a specific test result is indicative of a muscular disorder associated with a particular low back pain syndrome or whether it is consistent with muscle behavior of the normal, pain-free population. The EMG values from this test are entered into the formula and this formula categorizes the results as either low back pain or non-low back pain based on the data base used to develop the formula. A categorization of "low back pain" would mean that the subject's test resulted in measures of fatigability and muscle dysfunction that are typical of muscle disturbances in specific categories of back pain disorders (e.g. chronic low back pain, herniated intervertebral disc, other structural spinal disorders, etc.). The analysis procedure would also indicate to what degree of accuracy it was classifying a test result.

Obviously, many modifications and variations of the present invention are possible in light of the above teachings. For example, in addition to the disclosed technique for determining LBP, the system is readily applicable to evaluating muscle performance in most any situation in which multiple muscle groups (synergists or agonists/antagonists) are concurrently active to produce torque across a joint. The electrode array 13 would be applied to the different superficial muscle groups that function together during a particular fatigue-inducing task. The task would be defined and controlled in exactly the same way as in a back muscle evaluation. That is, the body part being tested would be constrained in a postural restraint device designed specifically for the body segment being tested. Force feedback and timing would be specified. All of the same parameters and methods of EMG and force analysis described for the BAS would be applied to evaluating the pattern of concurrent activity in the muscle groups being monitored. It is to be understood, therefore, that the invention can be practiced otherwise than as specifically described.

What is claimed is:

1. A muscle function analysis system comprising:
base means;
restraint means supported by said base means and shaped and arranged to receive and immobilize one portion of a human body, said one portion retaining a muscle group concurrently activatable to produce a body function and said restraint means comprising mold means shaped to conform to said one portion;
support means supported by said base means and shaped and arranged to support other portions of the body, said support means adapted to substantially isolate activity in said muscle group from muscle activity in said other portions of the body;
electrode means adapted for coupling to said muscle group so as to receive myoelectric signals generated by muscle activity therein; and
processing means coupled to said electrode means and adapted to process said myoelectric signals.

2. A muscle function analysis system according to claim 1 wherein said one portion comprises a body joint, said muscle group is activatable to produce torque controlling the position of said joint, and said restraint means establishes a predetermined angular orientation of said joint.

3. A muscle function analysis system according to claim 2 wherein said muscle group comprises a synergistic muscle group.

4. A muscle function analysis system according to claim 3 wherein said one portion of a human body is the pelvis, and said joint is between the pelvis and the torso.

5. A muscle function analysis system according to claim 4 wherein said mold means comprises plural molds adapted to envelop the hip, upper thigh, buttocks and anterior pelvic regions of the body.

6. A muscle function analysis system according to claim 5 wherein said mold means further comprises adjustable connector means for selectively fixing the relative positions between said plural molds.

7. A muscle function analysis system according to claim 4 wherein said restraint device is adapted to permit establishment of an adjustable posterior pelvic tilt.

8. A muscle function analysis system according to claim 7 wherein said support means comprises knee support means for supporting knees and foot support means for supporting feet.

9. A muscle function analysis system according to claim 8 wherein said knee support means is adapted to maintain the body's knee joints in flexion, and said foot support means is adapted to maintain the body's ankle joints in plantarflexion.

10. A muscle function analysis system according to claim 4 including force constraint means supported by said base means and adapted to engage and prevent movement of the body's torso during extension thereof.

11. A muscle function analysis system according to claim 10 wherein said constraint means comprises a flexible strap adapted to engage the body's back.

12. A muscle function analysis system according to claim 10 wherein said restraint device is adapted to permit establishment of an adjustable posterior pelvic tilt.

13. A muscle function analysis system according to claim 12 wherein said support means comprises knee support means for supporting knees and foot support means for supporting feet.

14. A muscle function analysis system according to claim 13 wherein said knee support means is adapted to maintain the body's knee joints in flexion, and said foot support means is adapted to maintain the body's ankle joints in plantarflexion.

15. A muscle function analysis system according to claim 6 wherein said base means comprises a substantially vertical standard portion and a pedestal portion adapted to support the body's feet.

16. A muscle function analysis system according to claim 15 wherein said restraint means comprises a first coupling providing a given spacing between said standard portion and an upper portion of said mold means and a second coupling providing a predetermined spacing between said standard portion and a lower portion of said mold means, and said given spacing is greater than said predetermined spacing.

17. A muscle function analysis system according to claim 16 wherein said restraint means comprises adjustment means for selectively adjusting said predetermined spacing relative to said given spacing.

18. A muscle function analysis system according to claim 16 wherein said support means comprises knee support means supported by said standard portion and defining knee support surfaces for supporting the body's knees and forming an acute angle with said standard portion so as to maintain the body's knee joints in flexion.

19. A muscle function analysis system according to claim 18 wherein said support means further comprises a foot support surface supported by said pedestal portion and inclined at an acute angle with respect to the horizontal so as to maintain the body's ankle joints in plantarflexion.

20. A muscle function analysis system according to claim 19 including force constraint means supported by said standard portion and adapted to engage and prevent movement of the body's torso during extension thereof.

21. A muscle function analysis system according to claim 20 wherein said constraint means comprises a flexible strap adapted to engage the body's back.

22. A muscle function analysis system according to claim 21 wherein said constraint means, said knee support means, and said restraint means are vertically adjustable on said standard portion.

* * * * *